United States Patent [19]

Pinnell

[11] Patent Number: 4,524,065

[45] Date of Patent: Jun. 18, 1985

[54] METHOD FOR THE PREVENTION AND TREATMENT OF SCARS WITH ENZYMES

[75] Inventor: Sheldon R. Pinnell, Durham, N.C.

[73] Assignee: Bio-Specifics N.V., Curacao, Netherlands Antilles

[21] Appl. No.: 520,203

[22] Filed: Aug. 4, 1983

[51] Int. Cl.³ .............................................. A61K 37/48
[52] U.S. Cl. ...................................................... 424/94
[58] Field of Search ........................................... 424/94

[56] References Cited

U.S. PATENT DOCUMENTS

| | | | |
|---|---|---|---|
| 3,678,158 | 7/1972 | Sussman | 424/94 |
| 3,705,083 | 12/1972 | Chiulli et al. | 424/94 |
| 4,174,389 | 11/1979 | Cope | 424/94 |
| 4,338,300 | 7/1982 | Gelbard | 424/94 |

OTHER PUBLICATIONS

Seifter, S., et al., In *Enzymes*, 3rd ed., pp. 649–697, 1971.
Lee, K. K., et al., Collagenase Therapy for Decubitus Ulcers, Genetics 30: 91, 1975.
Mazurek, T., In *Collagenase*, ed. Mandl, I., 1st ed., Gordon and Breach, Science Publishers, p. 171, 1970.
Zimmerman, W. E., In *Collagenase*, ed. Mandl, I., 1st ed., Gordon and Breach, Science Publishers, p. 131, 1970.
Sussman, B. M., et al., Injection of Collagenase in the Treatment of Herniated Lumbar Disk, JAMA 245: 730–732, 1981.
King, G. D., et al., Keloid Scars, Surg. Clin. N. Amer. 50: 595, 1970.
Lwebaga-Mukasa, P. Collagenase Enzymes from Clostridium: Characterization of Individual Enzymes, Biochemistry, 15: 4736, 1976.
Prugnaud et al.—Chem. Abst. vol. 78, (1973), p. 88621x.
Lee et al.-Geriatrics vol. 30, No. 91, (1975), pp. 91–93, 97 and 98.
Horton et al.-Plastic & Reconstructive Surgery, vol. 52, No. 503, (1973), pp. 503–510.

*Primary Examiner*—Sam Rosen
*Attorney, Agent, or Firm*—Roland Plottel

[57] ABSTRACT

A method for the prevention of and for the dissolution of mammalian cicatrices such as acne scars, keloids and other hypertrophic scars comprising intralesional injection of effective amounts of a pharmacologically suitable solution of the enzyme collagenase, by itself, and collagenase in combination with the enzyme hyaluronidase.

24 Claims, No Drawings

METHOD FOR THE PREVENTION AND TREATMENT OF SCARS WITH ENZYMES

BACKGROUND OF THE INVENTION

Collagen is the major structural constituent of mammalian organisms and makes up a large portion of the total protein content of skin and other parts of the animal body. In humans, it is particularly important in the wound healing process and in the process of natural aging. Various skin traumas such as burns, surgery, infection and accident are often characterized by the erratic accumulation of fibrous tissue rich in collagen and having increased proteoglycan content. In addition to the replacement of the normal tissue which has been damaged or destroyed, excessive and disfiguring deposits of new tissue sometimes form during the healing process. The excess collagen deposition has been attributed to a disturbance in the balance between collagen synthesis and collagen degradation.

Keloids are tumors of connective tissue consisting of highly hyperplastic masses which occur in the dermis and adjacent subcutaneous tissue in certain susceptible individuals, most commonly following trauma. The known therapies for keloids have had limited success and they frequently can recur in the site after surgical removal.

Hypertrophic scars are unsightly masses which can result from burns or other injuries to the skin. Such scars are usually permanent and resistant to known methods of therapy.

Depressed scars occur following inflammatory conditions and result in contraction of the skin, leaving a cosmetically unacceptable result. The most common example is the scarring which occurs following inflammatory acne. The condition is common and permanent. The depression occurs as a normal consequence of wound healing and the scar tissue causing the depression is predominantly composed of collagen.

Post-surgical adhesions sometimes form following surgery or inflammation, wherein the normal healing process may bind structures one to another. An undesirable example is the binding of tendons to tendon sheath. Such adhesions are common complications of surgery and no therapy is available. Collagen is a predominant part of this scarring process.

Acne vulgaris is another common skin disease often causing unsightly facial scars. Some acne patients have been successfully treated for acne scarring using intralesional steroids, liquid nitrogen, dermabrasion and the like. In many cases, however, the lesions do not respond or the treatment results in other complications.

Additional disfiguring conditions such as wrinkling, cellulite formation and neoplastic fibrosis also appear to result from excessive collagen deposition which produces unwanted binding and distortion of normal tissue architecture.

Enzymes are proteinaceous substances which act as catalysts for biological reactions; in some cases hydrolysis reactions and in others oxidation-reduction processes. Some enzymes have broad activity and others, such as collagenase (Clostridiopeptidase A) produced from the bacterium *clostridium hystolyticum*, have very specific activity. Highly purified collagenase has been prepared and been found uniquely capable of cleaving bonds in the collagen structure permitting other enzymes to act on the resulting molecular fragments.

The use of collagenase in medical practice is well known but has heretofore been limited to topical application for debridement of dermal ulcers and burns and, recently, for the treatment of prolapsed intervertebral discs. Purified collagenase has been demonstrated to be relatively safe even in large doses (thousands of units) in animals and in contact with human blood vessels, nerves and bones.

Hyaluronidase is a soluble enzyme product prepared from mammalian testes. It has been previously used in human medicine to increase the effect of local anesthetics and to permit wider infiltration of subcutaneously administered fluids.

SUMMARY OF THE INVENTION

The present invention comprehends the method of treating conditions in humans and animals associated with excessive fibrosis to restore normal appearance as well as the remodeling of unwanted fibrous tissue to obtain more acceptable cosmetic appearance by injecting directly into the disfiguring lesions an effective amount of the enzyme collagenase, by itself, or in combination with the enzyme hyaluronidase.

The present invention also includes the method of preventing the formation of disfiguring scars during the healing process following trauma which comprises administration of an effective amount of collagenase alone or collagenase in combination with hyaluronidase.

More particularly, it is the object of this invention to provide new, non-surgical and non-radical procedures for preventing and for treating objectionable cicatrices in animals and humans. It is believed that the use of enzymes in the prevention and treatment of disfiguring scars represents a significant advance in the art.

These and other objects and advantages of this invention will be apparent from the more detailed description which follows.

DESCRIPTION OF THE PREFERRED EMBODIMENTS

Purified collagenase, free of detectable caseinase and non-specific protease activity is manufactured by Advance Biofactures Corporation, Lynbrook, N.Y. The frozen enzyme is thawed and diluted with normal saline solution plus 2 mM calcium chloride to the desired concentration. Enzyme activity, given in ABC units, is determined using an insoluble substrate, undenatured bovine tendon, according to a modification of the method of Mandl et al (Arch Biochem Biophys 74:465–475, 1958). A unit of activity corresponds to the release of ninhydrin reactive material equivalent to nanomoles leucine equivalents released in one minute from undenatured collagen. Collagenase is obtained from culture of a special strain of *clostridium histolyticum* and purified by a chromatographic technique.

Hyaluronidase (Wydase) is manufactured by Wyeth Laboratories, Philadelphia, Pa. It is a preparation of highly purified bovine testicular hyaluronidase and is available dehydrated in the frozen state under high vacuum. The N.F. Hyaluronidase Unit is equivalent to the turbidity-reducing (TR) unit and the International Unit.

The following Examples are presented for the purpose of illustrating the invention:

EXAMPLE I

A male patient with an abdominal keloid resulting from an old surgical procedure is medically screened and found qualified for enzyme therapy. The patient receives four injections, 0.1 ml. each, containing 50, 100, 250 and 500 units of collagenase respectively, directly into the lesion. The patient is observed for one hour after the injections for allergic reactions or other effects. The patient returns after one month for laboratory work and assessment of the concentration giving him the best therapeutic response. He thereafter receives additional injections of the optimum concentration at appropriate intervals until the desired keloid size reduction is achieved.

EXAMPLE II

A male patient with a disfiguring hypertrophic scar, resulting from an earlier trauma, is medically screened and found suitable for enzyme therapy. The scar is multiply injected with 250 units of collagenase combined with 150 units of hyaluronidase in a total volume of 0.2 ml. per injection. Further intralegional injections of the same components and concentrations are given at monthly intervals. Therapy is terminated when the desired reduction in scar size is achieved or failure of improvement between treatments is noted.

EXAMPLE III

A female patient with a prior history of disfiguring surgical scar formation is examined during convalescence from surgery and found to be producing keloidal tissue in the new incision. She is medically screened and found otherwise suitable for enzyme therapy. Multiple intralesional injections of 50 units of collagenase combined with 150 units of hyaluronidase in a total volume of 0.2 ml. per injection are made at one week intervals. Therapy is discontinued when scar healing is completed or when no further improvement in scar architecture is noted.

EXAMPLE IV

A female patient with multiple acne scars of both closed comedo-like character and "ice-pick" type is medically screened and found suitable for enzyme therapy. The scars are injected with 100 units of collagenase in a total volume of 0.1 ml. per injection. The patient returns after one month for laboratory tests and evaluation of the clinical response. The total number of treatment visits is six or fewer to achieve substantial improvement in overall skin contour.

EXAMPLE V

A female patient with depressions on her thighs caused by fibrotic bands in the fatty connective tissue, commonly called cellulite, is medically screened and found suitable for enzyme therapy. Multiple injections of 100 units of collagenase combined with 150 units of hyaluronidase in a total volume of 0.2 ml. per injection are made in the affected area. Therapy continues at intervals of two weeks until the desired improvement in skin contour is achieved.

In view of the preceding description, further modifications and alternative embodiments of the instant invention will be apparent to those skilled in the art. Accordingly, the preceding descriptions and examples are to be construed as explanatory and illustrative only and are for the purpose of teaching and enabling those skilled in the art to practice this invention. It should be understood that the amount of the pharmacologically suitable solution of enzymes required for the dissolution of mammalian cicatrices will vary. Suitable amounts can be determined from a reasonable number of experiments and the following factors should be considered: the nature of the cicatrix being treated, the concentration of collagenase and hyaluronidase, if any, in the solution, the type of collagenase used, the amount, location and nature of the collagen fibers to be dissolved as well as the nature of the tissue adjacent to the cicatrix being treated.

While the preferred embodiment of the above described invention is to be understood to be the best mode presently contemplated, it is by no means the only embodiment possible. The scope of the invention is defined by the following claims and by any equivalent modifications and variations that fall within the true spirit of the invention.

What is claimed is:

1. A method for the dissolution of mammalian cicatrices which comprises administering an effective amount of the enzyme collagenase directly into the lesion.

2. The method of claim 1 wherein the collagenase is a culture of a special strain of *clostridium histolyticum* chromatographically purified to be free of detectable protease activity.

3. The method of claim 1 wherein the collagenase is administered in the range of 50 to 500 units.

4. The method of claim 1 wherein the collagenase is administered in a series of intralesional injections at spaced time intervals.

5. The method of claim 1 wherein the cicatrix is a keloid.

6. The method of claim 1 wherein the cicatrix is a hypertrophic scar.

7. The method of claim 1 wherein the cicatrix is an acne scar.

8. The method of claim 1 wherein the cicatrix is a depressed scar.

9. The method of claim 1 wherein the cicatrix is a wrinkle.

10. The method of claim 1 wherein the cicatrix is cellulite.

11. The method of claim 1 wherein the cicatrix is neoplastic fibrosis.

12. A method for the dissolution of mammalian cicatrices which comprises administering an effective amount of the enzyme collagenase in combination with an effective amount of the enzyme hyaluronidase directly into the lesion.

13. The method of claim 12 wherein the collagenase is administered in the range of 50 to 500 units in combination with hyaluronidase in the range of 25 to 250 units.

14. The method of claim 12 wherein the cicatrix is a keloid.

15. The method of claim 12 wherein the cicatrix is a hypertrophic scar.

16. The method of claim 12 wherein the cicatrix is an acne scar.

17. The method of claim 12 wherein the cicatrix is a depressed scar.

18. The method of claim 12 wherein the cicatrix is a wrinkle.

19. The method of claim 12 wherein the cicatrix is cellulite.

20. The method of claim 12 wherein the cicatrix is neoplastic fibrosis.

21. A method for the prevention of mammalian cicatrices which comprises administering an effective amount of the enzyme collagenase directly into the affected area during the healing process.

22. The method of claim 21 wherein the collagenase is administered in the range of 50 to 500 units.

23. A method for the prevention of mammalian cicatrices which comprises administering an effective amount of the enzyme collagenase in combination with an effective amount of the enzyme hyaluronidase directly into the affected area during the healing process.

24. The method of claim 23 wherein the collagenase is administered in the range of 50 to 500 units in combination with hyaluronidase in the range of 25 to 250 units.

* * * * *